United States Patent [19]
Rice et al.

[11] Patent Number: 5,821,340
[45] Date of Patent: Oct. 13, 1998

[54] INDUCIBLE ENDOTHELIAL SURFACE PROTEIN MEDIATING LYMPHOID AND TUMOR CELL ADHESION: ANTIBODIES AND USES

[75] Inventors: G. Edgar Rice, Boston; Michael P. Bevilacqua, Holbrook, both of Mass.

[73] Assignee: Brigham & Women's Hospital, Boston, Mass.

[21] Appl. No.: 310,201

[22] Filed: Feb. 14, 1989

[51] Int. Cl.⁶ ............................... C12N 5/12; C07K 16/41
[52] U.S. Cl. .................... 530/388.2; 435/240.27; 530/391.7; 530/388.22; 530/388.7
[58] Field of Search ...................... 530/387–389, 530/388.22, 391.7, 388.7; 435/240.27

[56] References Cited

PUBLICATIONS

Rice et al, "Tumor Cell–Endothelial interactions", vol. 133, No. 2, pp. 204–209, Nov. 1988.
Bevilacqua et al, "Identification of an Inducible Endothelial–Leukocyte Adhesion Molecule", vol. 84, pp. 9238–9242, Dec. 1987.
Prober et al, "Two Distinct Monokines, Interleukin 1 and Tumeor Necrosis Factor, Each Independently Induce Biosynthesis and Transient Expression of the Same Antigen on the Surface of Cultured Human Vascular Endothelial Cells", vol. 136, No. 5, pp. 1680–1687, Mar., 1986.
Dejana et al, "Interleukin 1 Promotes Tumor Cell Adhesion to Cultured human Endothelial Cells", vol. 82, pp. 1466–1470, Oct., 1988.
Dustin et al, "Lymphocyte Function– Associated Antigen–1 (LFA–1) Interaction with Intercellular Adhesion Molecule–1 (ICAM–1) is One of at Least Three Mechanisms for Lymphocyte Adhesion to Cultured Endothelial Cells Mechanisms for Lymphocyte Adhesion to Cultured Endothelial Cells", vol. 107, pp. 321–331, Jul., 1988.

Rothlein et al, "A Human Intercellular Adhesion Molecule (ICAM1) Distinct From LFA–1", vol. 137, No. 4, pp. 1270–1274, Aug., 1986.
Staution et al, "Primary Structure of ICAM–1 Demonstrates Interaction Between Members of the Immunoglobulin and Integrin Superqene Families", vol. 52, pp. 925–933, Mar. 25, 1988.
Marlin et al., "Purified Intercellular Adhesion Molecule–1 (ICAM–1) is a Ligand for Lymphocyte Function–Associated Antigen LFA–1)", vol. 51, pp. 813–819, Dec., 1987.
Varani et al, "Adhesive Characteristics of Tumor Cell Variants of High and Low Tumorigenic Potential", vol. 64, No. 5, pp. 1173–1178, May, 1980.
Bevilacqua et al, "Interleukin 1 Acts on Cultured Human Vascular Endothelium to Increase the Adhesion of Polymorphonuclear Leukocytes, Monocytes, and Related Leukocyte Cell Lines", vol. 76, pp. 2003–2011, Nov., 1985.
Bevilacqua et al, "Experimental Pathologist–in –Training Award" vol. 121, pp. 394–403, (1980).
Bevilacqua et al, "Endothelial–Dependent Mechanisms of Leukocyte Adhesion: Regulation by Interleukin–1 and Tumor Necrosis Factor" pp. 79–93, 1986.

*Primary Examiner*—Lila Feisee
*Attorney, Agent, or Firm*—Leydig, Voit & Mayer, Ltd.

[57] ABSTRACT

Monoclonal antibody E1/6, or a fragment thereof, identifies a cytokine-inducible 110 kilodalton endothelial cell glycoprotein and blocks adhesion to vascular endothelial cells of certain blood leukocytes and tumor cells in vitro.

4 Claims, 4 Drawing Sheets

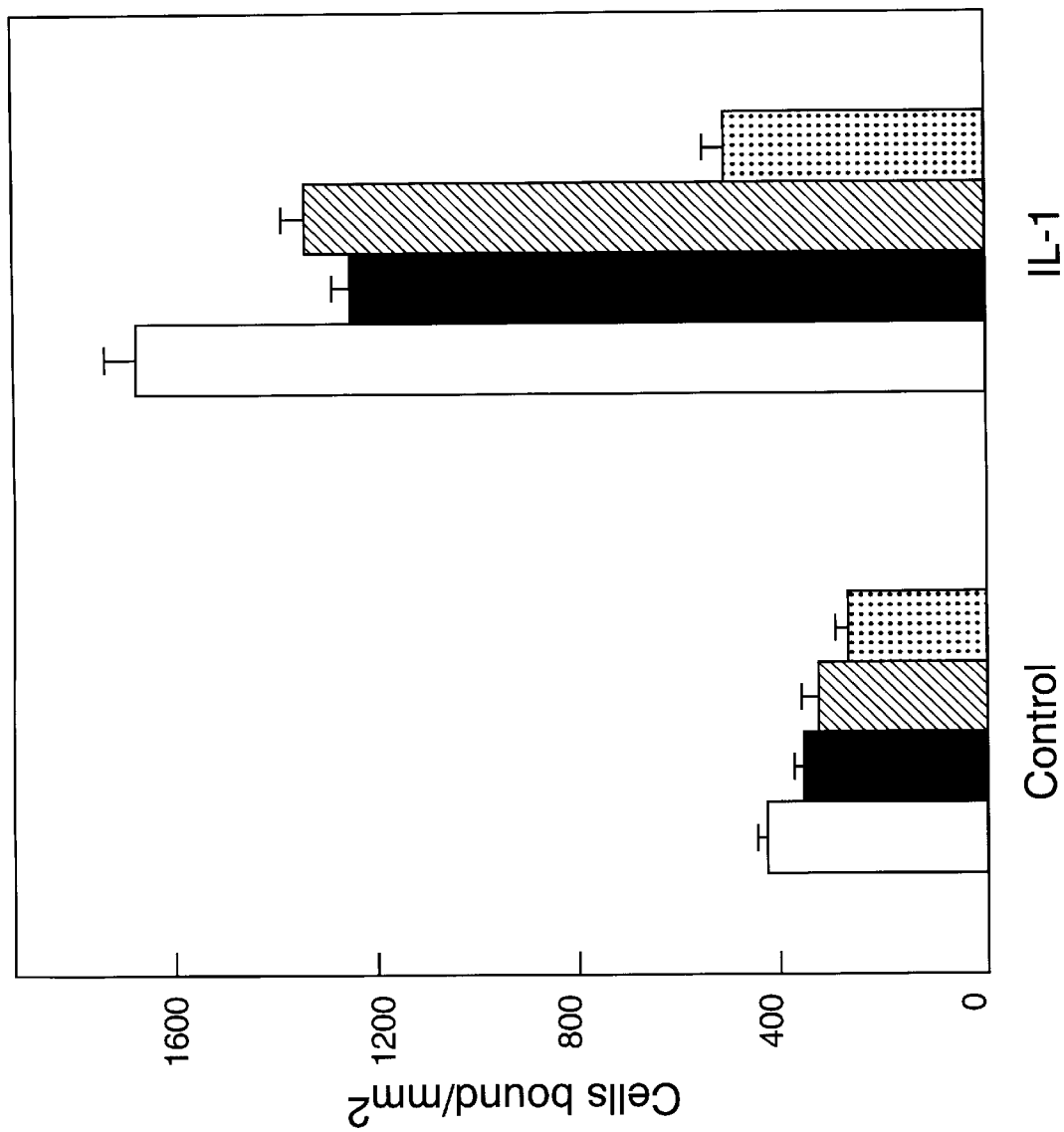

and tumor cell adhesion: antibodies
and uses

INDUCIBLE ENDOTHELIAL SURFACE PROTEIN MEDIATING LYMPHOID AND TUMOR CELL ADHESION: ANTIBODIES AND USES

The U.S. Government has rights in this invention pursuant to a grant or grants from the National Institutes of Health.

FIELD OF THE INVENTION

An inducible endothelial cell surface molecule is identified and characterized. This antigen is also found on certain dendritic cells and macrophages known to be involved in immunological reactions, including antigen presentation. Monoclonal antibody E1/6 generated from this molecule blocks adhesion of human lymphocytes, lymphoma cells and non-lymphoid tumor cells (e.g. melanoma cells) to endothelial cells. E1/6 and its corresponding glycoprotein are used in pharmaceutical, therapeutic and diagnostic protocols.

BACKGROUND OF THE INVENTION

Vascular endothelium constitutes the innermost lining of blood vessels. In this key anatomic position it may play an essential role in a variety of pathophysiological processes, including thrombosis, inflammation, immune responses, and tumor cell metastasis. In particular, vascular endothelium has been shown to play an active role in the adhesion of blood leukocytes (neutrophils, monocytes, and lymphocytes), presentation of antigen to lymphocytes, and contribution to the binding of nonlymphoid tumor cells. Recent evidence suggests that specific endothelial cell surface molecules are involved in these processes. For example, endothelial-leukocyte adhesion molecule-1 (ELAM-1) is an inducibe $M_r$ 115,000 glycoprotein found on the surface of activated endothelial cells that mediates the adhesion of blood neutrophils. Through this function, ELAM-1 appears to play a central role in mediating neutrophil influx into sites of acute inflammatory processes. The invention described herein (monoclonal antibody E1/6 and the glycoprotein recognized by the antibody) relates functionally to the attachment of both normal and neoplastic lymphocytes, and certain nonlymphoid tumor cells (e.g. melanoma) to endothelium.

In the development of an immune response, a foreign antigen must be processed and "presented" to lymphocytes in combination with MHC molecules by a second cell designated as "antigen presenting". A number of cell types have been implicated in the process of antigen presentation. Experimental evidence suggests that certain dentritic cell populations of lymphoid tissue and elsewhere, endothelial cells, and macrophages can function as antigen presenting cells. Studies of antibody binding using human tissues and an immunoperoxidase technique reveal that E1/6 antigen is expressed on endothelium, dendritic cell populations, and in certain tissue macrophages (e.g. Kupffer cells of the liver), as well as Bowman's epithelium of the kidney. Given such a distribution, and function as a lymphoid cell adhesion molecule, E1/6 antigen may play a key role in a variety of inflammatory and immunological responses (e.g. antigen presentation and graft rejection). As further described below, the ability of antibody E1/6 to block tumor cell adhesion to endothelium also suggests a role in the process of hematogenous metastasis.

Endothelium, the cells which line blood vessels and lymphatics, constitutes the first anatomic barrier between circulating tumor cells (and tumor subpopulations) and extravascular tissue (a process called extravasation). Thus, adhesion of tumor cells to the endothelium plays a role in hematogenous metastasis, a multi-stage phenomena that includes the distribution and interaction of blood-borne tumor cells with blood vessel walls. Although various tumor cells have been shown to adhere to endothelial monolayers in vitro, early observations indicated that the subendothelial matrix, a part of the microvasculature, is generally more adhesive for tumor cells than unstimulated endothelial cells themselves.

In vivo, localized modulation of the surface adhesive properties of vascular endothelium may influence the first step in tumor implantation, thus potentially affecting the incidence or pattern of hematogenous metastasis. Hematogenous metastasis is in itself an inefficient process, with the great majority of tumor cells failing to survive the circulation, in part due to the endothelium's ability to act as a barrier to extravasation. However, in vivo observations indicate that certain tumor cells directly adhere to intact endothelium, and subsequently transmigrate to contact the basal lamina, often after many hours. In short, the ability of circulating tumor cells to traverse the vascular endothelial lining may be a key factor in determining the ultimate survival and metatastatic capacity of the tumor cell.

Focal adhesion of blood-borne tumor cells and blood leucocytes to the vascular lining is a key step in a variety of pathophysiological processes, including hematogenous metastasis, inflammation, tissue repair, and other pathophysiological processes involving endothelial activation. Bacterial endotoxin and multifunctional (inflammatory/immune) cytokines, such as interleukin-1 and tumor necrosis factor (TNF), can act directly on cultured human endothelial cell (HEC) monolayers, in a time- and protein synthesis-dependent fashion, to increase the adhesion of certain human melanoma and carcinoma cell lines. These mediators can act directly on HEC monolayers to increase the adhesion of blood leukocytes and leukocyte cell lines. This effect is mediated, at least in part, through the synthesis and expression of specific endothelial cell surface proteins that bind leukocytes.

Vascular endothelial cells of various organs preferentially bind certain tumor cells, and display different cell surface components.

Recent studies suggest that activation of cultured human umbilical vein endothelial cells (HEC) also increase the adhesion of certain other cancer cells, such as carcinoma cell lines, suggesting that E1/6 protein or similar molecules may play an important role in the metastasis of many cancer cell types.

Since the expression of E1/6 protein can be modulated by soluble mediators, localized and transient changes in expression may occur in a variety of pathophysiological processes. In addition, the production within a vessel of cytokines by tumor cells themselves could potentially lead to upregulation of adhesion molecules on adjacent endothelium, thereby influencing extravasation, the discharge of blood cells outside the vascular sytem.

E1/6 protein is expressed by vascular endothelium in human lung, skin, brain and lymphoid tissue in vivo, and its increased expression is evident in sites of certain pathophysiological processes involving endothelial activation. E1/6 protein appears to play a major role in melanoma-endothelial cell adhesion and, thus, may contribute to the development and distribution of metastatic lesions.

Endothelial cell surface properties can be modulated by a number of stimuli in vitro, including coagulation factors (e.g. thrombin), inflammatory/immune cytokines, and extracellular matrix components. Activation of endothelium by interleukin-1 (IL-1) and tumor necrosis factor (TNF) induces the biosynthesis and expression of cell surface molecules that mediate the adhesion of blood leukocytes. Endothelial-leukocyte adhesion molecule-1 (ELAM-1), a $M_r$ 115,000 glycoprotein expressed by activated endothelium, acts as a receptor for polymorphonuclear leukocytes. Intercellular adhesion molecule-1 (ICAM-1) is a $M_r$ 90,000 glycoprotein expressed by both leukocytic and non-leukocytic cell types and contributes to a variety of cell—cell adhesive interactions including lymphocyte aggregation, lymphocyte-fibroblast adhesion, and leukocyte-endothelial adhesion.

Monoclonal antibodies (Mab) that bind to ELAM-1 were generated against IL-1 or TNF-stimulated HEC and were found to react with the same inducible cell surface protein (Mr 115,000) present on cytokine-stimulated HEC, but not on unstimulated HEC. One of these Mab, H18/7, significantly inhibits the adhesion of human neutrophils and HL-60 cells to stimulated HEC, supporting the designation endothelial-leukocyte adhesion molecule-1 (ELAM-1). A full length cDNA encoding ELAM-1 has been isolated by transient expression in COS cells. Cells transfected with this cDNA express a surface glycoprotein recognized by Mab H4/18 and H18/7 and support the adhesion of neutrophils and HL-60 cells.

ELAM-1 is an inducible endothelial cell surface glycoprotein structurally related to complement regulatory protein (e.g. complement receptor 1) and to lectin-like molecules (e.g. asaialoglycoprotein receptor). The expression of ELAM-1 is essentially restricted to activated endothelium. ICAM-1, a member of the immunoglobulin supergene family, is found at low levels on unstimulated endothelium in vitro and in vivo. ICAM-1 is also present on a variety of lymphoid and nonlymphoid cell types. Assessment of potential relationships between E1/6 protein and ELAM-1 or ICAM-1 awaits determination of its primary structure. Two other endothelial adhesion molecules, the vascular addressins, are constitutively expressed on high endothelial venules of lymphoid tissues and play a role in lymphocyte homing. These addressins may be representative of organ specific structures postulated to be involved in tumor metastasis. However, to date, organ specific molecules that mediate adhesion of nonlymphoid tumor cells have not been identified.

Monoclonal antibody E1/6 was first observed to block endothelial cell-melanoma cell adhesion, whereas monoclonal antibodies to two other inducible molecules, ELAM-1 and ICAM-1, had no significant effect.

In short, functional and immunochemical characterizations show that E1/6 mAb and antigen are distinct from ELAM-1, ICAM-1, and ICAM-2.

SUMMARY OF THE INVENTION

The present invention involves the identification and initial characterization of an inducible endothelial cell surface molecule involved in the adhesion of human lymphoytes, lymphoid tumor cells, and non-lymphoid tumor cells (melanoma cells). This protein is also found on dendritic cell populations and macrophages known to be involved in imunological processes including antigen presentation.

The monoclonal antibody of the present invention, mAb E1/6, which recognizes a Mr 110,000 inducible endothelial surface glycoprotein, inhibits the adhesion of several melanoma cell lines (>70%). mAb E1/6, generated against cytokine-activated HEC, was found to react with an inducible endothelial structure, the expression of which parallels melanoma adhesion.

It is an object of the present invention to characterize an inducible endothelial surface protein capable of mediating cancer cell (e.g. melanoma cell) adhesion.

Another object is to provide a monoclonal antibody which significantly blocks adhesion of certain B and T cell lymphoma lines to the endothelial cells.

Another object is to provide a monoclonal antibody which can be used in examining the expression of E1/6 protein in vitro to determine the altered expression of the E1/6 protein and its relationship to specific disease processes.

Another object is to provide a monoclonal antibody which recognizes a dendritic cell population in lymph nodes and papillary dermis.

Another object is to provide a diagnostic reagent capable of localizing sites of altered endothelium.

Another object is to provide a diagnostic reagent capable of identifying normal or aberrant phenomena in embryological development.

Another object is to provide a diagnostic reagent capable of staining pathological vascular endothelium.

Another object is to provide monoclonal antibodies to mark tissues or molecules for use in cancer imaging and therapy, neutron capture therapy, positron emission tomography (PET), magnetic resonance imaging (MRI), and electron microscopy (EM).

Another object is the use of monoclonal antibody E1/6, or a fragment thereof, in the detection of endothelial cell activation, comprising (a) bringing into contact a biological sample suspected of containing activated endothelial cells with mAb E1/6 and (b) detecting whether a complex has formed.

RELEVANT LITERATURE

Pober, et al., *J. Immunol.*, 136:1680 (1986) disclose a method for producing a monoclonal antibody which recognizes an antigen on the surface of activated vascular endothelial cells.

Bevilacqua, et al., *PNAS, USA,* 84:9238 (1987) disclose the identification of an enducible endothelial-leukocyte adhesion molecule (ELAM-1), and the production of monoclonal antibodies to this molecule.

Rice, et al., *FASEB J.*, 2:A1407 (1988); Rice, et al., *Amer. J. Path.*, 133:204 (1988); and Dejana, et al., *J. Clin. Invest.*, 82:1466 (1988) disclose that human melanoma cell lines exhibit increased adhesion to activated endothelium. These publications suggest that inducible endothelial cell surface structures may mediate the adhesion of certain melanoma cells, thereby affecting metastatic processes.

Rothlein, et al., *J. Immunol.*, 137:1270 (1986) disclose the identification of a human intercellular adhesion molecule (ICAM-1).

Dustin, et al., *J. Cell Biol.*, 107:321 (1988) disclose the contribution of ICAM-1 to a variety of cell—cell adhesive interactions.

Certain inflammatory/immune cytokines including interleukin-1 (IL-1) and tumor necrosis factor (TNF), as well as bacterial endotoxin, have been shown to act directly on cultered human vascular endothelium to increase the adhesiveness of its surface for blood leukocytes and related cell lines. Bevilacqua, M. P. et al., *J. Clinical Invest.*

76:2003–2011 (1985); Bevilacqua, M. P. et al., *Am. J. Pathology* 121:393–403 (1985); Bevilacqua, M. P. et al., *Leukocyte Emigration and its Sequelae*, Movat, H. Z. (ed.), Karger, N.Y. pp. 79–93 (1987) Bevilacqua et al., *Proc. Natl. Acad. Sci., (USA)* 84: 9238–9242, 1987; Gamble, J. R. et al., *Proc. Natl. Acad. Sci.(USA)* 82:8667–8671 (1985); Schleimer, R. P. et al., *J. Immunol.* 136: 649–654 (1986); Dunn, C. J. et al., *The Physiologic, Metabolic and Immunologic Actions of Interleukin-1*; Kluger, M. J. et al., *J. Immunol.* 136:203–207 (1986); Yu, C.-L. et al., *J. Immunol.* 136:571 (1986); and Polhlman, T. H. et al., *J. Immunol.* 136:4548–4553 (1986).

It has been shown that whole antibodies can be labeled with radioisotopes and used for the detection of cancer in humans (Burchiel, et al., U.S. Pat. No. 4,311,688; Carlsson, et al., U.S. Pat. No. 4,232,119).

It has also been shown that the Fab portion of an immunoglobulin can be labeled and used in diagnostic and detection regimens (Sjoquist, et al., U.S. Pat. No. 3,966,898; Ling, U.S. Pat. No. 4,298,593).

It has also been shown that metal chelates can be conjugated to monoclonal antibodies and used in diagnostic and therapeutic techniques (Gansow, et al., U.S. Pat. Nos. 4,454,106 and 4,472,509).

It has also been shown that electron dense moieties, such as ferritin [Singer, *Nature*, 183:1523 (1959)] or colloidal gold [De Mey et al, U.S. Pat. No. 4,446,238 and Faulk et al *Immunochemistry*, 8:1081 (1971)], can be used as markers for visualization of antibody labels in the electron microscope.

DESCRIPTION OF THE FIGURES

FIG. 4 shows that adhesion of peripheral blood lymphocytes is blocked by E1/6 mAb.

DETAILED DESCRIPTION OF THE INVENTION

Figure 1:
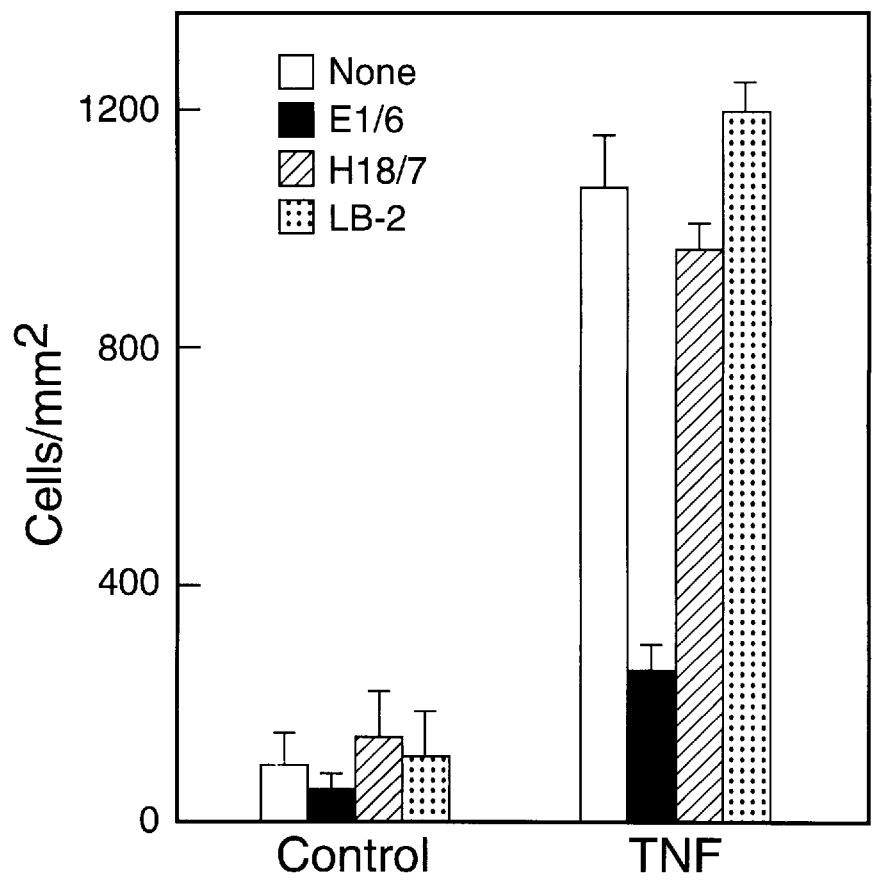
FIG. 1 shows the effect of mAbs E1/6, H18/7 (anti-ELAM-1), and LB-2 (anti-ICAM-1) on MEL-24 cell adhesion to HEC. Bars represent mean +/− SEM of quadruplicate microtiter wells in one of four similar experiments.

The present invention involves reagents and compositions that are suitable for use in diagnosis of certain pathophysiological processes that involve endothelial cell activation, mediation, or adhesion to lymphocytes, lymphoid tumor cells, and non-lymphoid tumor cells (e.g. melanoma cells). These cells include but are not limited to melanoma, leukocytes, lymphoma, leukemia, and certain interactions or infections caused by microbial organisms. Disorders which involve endothelial cell adhesion include but are not limited to inflammation, including acute and chronic inflammatory diseases immune reactions, such as lupus erythematosus, vasculitis, demyelinating diseases, and graft rejection, MONOCLONAL ANTIBODY E1/6.

The E1/6 monoclonal antibody (E1/6 mAb) may be produced using well known techniques such as that disclosed by Kohler, et al, in *Nature*, 256:495–497(1975). Practitioners in the art will recognize that variation of the K-M technique and other methods may be used to produce the mAbs of the subject invention. A useful reference for obtaining monoclonal antibodies is Koprowski et al, U.S. Pat. No. 4,196,265.

E1/6 antibodies may be prepared by immunizing mice with cultured human endothelial cells (HEC) which have been activated by a cytokine, for example, the monokine interleukin 1 (IL 1). Fusion of the splenocytes with myeloma cells and subsequent screening of the hybridomas with IL 1-treated and control HEC allows selection of E1/6 monoclonal antibodies. See Bevilacqua, M. P., et al., *4th Int'l Symp. Biol. Vasc. Endothelial Cell:*13 (Abstr) (1986); Pober, J. S., et al., *J. Immunol.* 136:1680–1687 (1986); Bevilacqua, M. P., et al., in: *Leukocyte Immigration and Its Sequelae, Satellite Symp.* (Henry Z. Movat, ed.), pp. 79–93, published by S. Karger, Basil, Switzerland (1987). The E1/6 hybridoma was deposited with the *American Type Culture* Collection (ATCC), 12301 Parklawn Drive, Rockville, Md. 20852 on Aug. 27, 1992, and given accession number HB 11105.

As shown in Example 1, E1/6 mAb recognizes an inducible endothelial cell surface glycoprotein ($M_r$ 110,000) that may mediate the adhesion of melanoma cells and peripheral blood lymphocytes to mammalian (including human) vascular endothelial cells, particularly of the lung, lymph, and skin. E1/6 mAb also precipitates an endothelial protein of $M_r$ 110,000, a protein that is distinct from other adhesion molecules such as ELAM-1 and ICAM-1. E1/6 mAb also recognizes populations of dendritic cells (antigen presenting cells) in the intra- and inter-follicular areas of lymphoid tissue (e.g., tonsil) and in the papillary dermis of the skin. E1/6 mAb also recognizes Bowman's epithelium of the kidney.

Pooled hybridoma culture supernatants (RPMI-10% horse serum) containing quantities of E1/6 mAbs sufficient to saturate HEC surface binding sites inhibited the adhesion of melanoma cells (HS 294T) to TNF-activated endothelial monolayers.

The monoclonal antibody of the present invention, mAb E1/6, generated against cytokine-activated HEC, was found to react with an inducible endothelial structure, the expression of which parallels melanoma adhesion: adhesion is low on unstimulated HEC, but increases on cytokine-stimulated HEC (maximum 6–8 hr, maintained >24 hr). E1/6 mAb significantly inhibits (50–90%) adhesion of melanoma cell lines to activated HEC (see Examples 3 and 4). However, antibody E1/6 does not block adhesion of the human colon carcinoma cell line HT-29.

Potential uses of MAb E1/6 or portions thereof include: (1) blocking tumor cell-endothelial adhesion in vivo, thereby inhibiting metastasis, (2) blocking lymphocyte-endothelial adhesion in vivo, thereby inhibiting or otherwise modifying inflammatory or immune reaction, (3) blocking lymphoma or leukemia interactions with vascular endothelium, thereby inhibiting tissue spread, (4) localizing sites of altered endothelium in diagnostic studies, (5) examining the expression of E1/6 protein and various tissue specimens in vitro to determine altered expression of this molecule, which may be associated with specific disease processes, (6) treating infections with microorganisms that may interact with or infect vascular endothelium after binding to E1/6 protein, by interrupting the microbial interaction with vascular endothelium, (7) used alone or coupled to cytotoxic agents, the tumor growth, (8) identifying normal or abberrant phenomena in embryological development, and (9) blocking of lymphocyte interactions with dendritic cells, macrophages, or other immune cells, thereby inhibiting immunological responses.

E1/6 mAb may also be used to detect a dendritic cell population in lymph nodes and skin; to detect certain activated B-lymphocytes; and in the staining of vascular endothelium in a variety of diagnostic processes.

E1/6 mAbs are generally maintained in an aqueous solution that contains an ionic compound. A physiologic normal saline is preferred and widely available. Other ionic solutions, such as those containing sodium or potassium phosphate, sodium carbonate and the like, are known in the art and may also be used in the practice of this invention.

"Antibody" is a term of art denoting the soluble substance or molecule secreted or produced by an animal in response to an antigen, and which has the particular property of combining specifically with the antigen that induced its formation. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds). When IgG is treated with the enzyme papain, an antigen binding fragment can be isolated, termed Fab. When IgG is treated with pepsin (another proteolytic enzyme), a larger fragment is produced, F(ab')$_2$. This fragment can be split in half by reduction to Fab'. The Fab' fragment is slightly larger than the Fab and contains one or more free sulfhydryls from the hinge region (which are not found in the smaller Fab fragment). It is known in the art that Fab' fragments can be prepared that have one free sulfhydryl group at a location distant from the antibody-antigen binding region. See Martin et al, *Biochemistry*, 20:4229 (1981).

The term "antibody fragment" is used herein to define the portion known as Fab' or F(ab')$_2$. It is well known in the art to treat antibody molecules with pepsin in order to produce antibody fragments [Gorevic et al, *Methods of Enzymol.*, 116:3 (1985)]. The term "immunochemical reaction" is used to denote the specific interaction which occurs between an antigen and its corresponding antibody.

Included within the scope of this invention is conjugating mAb E1/6, or a fragment thereof, to a chelate. The chelate-conjugated monoclonal antibody is formed by adding a chelate, for example [(diethylenetriamine pentaacetic acid) dicyclic anhydride)] (DTPA), in an organic solvent to an aqueous saline antibody solution. It is important to carry out the reaction of the modified DTPA and antibody at a pH not higher than about 7.2 The chelate-antibody reaction competes with the decomposition of the chelate caused by its reaction with water. If the pH is too low, however, the chelate undergoes acid catalysed decomposition and the biological activity and specificity of the antibody is diminished. The pH is desirably in the range of from about 6.0 to about 7.2, preferably as close to 7.0 as practicable. In this range, the reaction of the DTPA chelate with water is less detrimental to the chelate-antibody reaction.

While the above discussion has focused on DTPA, it is within the skill of the art to form conjugates, employing other ligands. See, e.g., *PNAS, USA*, 73:3803 (1976).

A wide variety of organic chelating agents or ligands can be conjugated to the monoclonal antibody of the present invention. Organic ligands to be conjugated to monoclonal antibodies may be chosen from among either the natural or synthetic amines, porphyrins, aminocarboxylic acids, iminocarboxylic acids, ethers, thiols, phenols, glycols and alcohols or the polyamines, polyaminocarboxylic acids, polyiminocarboxylic acids, aminopolycarboxylic acids, iminopolycarboxylic acids, nitrilocarboxylic acids, trilopolycarboxylic acid, polynitrilopolycarboxylic acids, ethylenediaminetetracetates, diethylenetriaminepenta or tetracetates, polyethers, polythiols, cryptands, polyetherphenolates, polyetherthiols, ethers of thioglycols or alcohols, polyaminephenols, all either acyclic, macrocyclic, cyclic, macrobicyclic or polycyclic, or other similar ligands which produce highly stable metal chelates or cryptates. Chelating agents include, but are not limited to, CYEDTA (trans-1,2-diaminocyclohexane-N,N,N',N'-tetraacetic acid) dianhydride, aminopolycarboxylates, tartrate, citrate, EDTA, IDA, TETA, bleomycin, and bromotrimethyl HIDA. All of these chelating agents may be used in various buffers well known to the practitioner.

To preserve the maximum biological activity of the antibody, the use of strong acids or bases to adjust pH should be avoided for any chelate-antibody preparation. Use of a strong acid or base can cause localized denaturation in the solution. The pH can be controlled in the aqueous solution of monoclonal antibody by including a suitable buffer. For example, NaHCO$_3$ at a concentration of approximately 0.1M can be used. Other buffers such as MES (2-(N-morpholino) ethane sulfonic acid) are known in the art and may also be employed. The choice of an appropriate buffer is within the skill of the art. Obviously, the choice of the ligand depends upon the end use, a decision which is well within the skill of the art.

The ligand used in certain embodiments of this invention possesses a nonmetal bonded organic functional group suitable for bonding to the monoclonal antibody. Functional groups may be chosen from among the carboxylic acid groups, diazotiazable amine groups, succidates, nitrenes, isothiocyanates, azides, sulfonamides, bromacetamides, iodoacetamides, carbodimides, sulfonylchlorides, hydrazides, thioglycols, or any reactive functional group known in the art as a biomolecular conjugating or coupling agent.

E1/6 ANTIGEN

The E1/6 protein is expressed at low levels in unstimulated endothelium in vitro and in vivo. Its expression can be dramatically increased by activating the endothelium with specific cytokines (e.g., IL-1, TNF, and interferon gamma) and bacterial endotoxin. The expressed E1/6 protein, or fragment thereof, may be isolated from cell lysates or possible cell culture supernatants, and purified in accordance with conventional procedures, such as extraction, precipitation, chromatography, affinity chromatography, electrophoresis, and the like. For example, E1/6 protein may be purified by passing a solution containing the protein through a column containing an immobilized antibody that is specific for the E1/6 protein. An example of a suitable antibody is the E1/6 mAb described above. The desired protein may then be eluted by raising the pH of the eluant.

Purified E1/6 protein, or portions thereof, may be useful for: (1) blocking tumor cell-endothelial adhesion in vivo, thereby inhibiting metastasis, (2) blocking lymphocyte-endothelial adhesion and/or lymphocyte-dendritic cell adhesion in vivo, thereby inhibiting or otherwise modifying inflammatory or immune reactions, (3) binding directly to non-lymphoid tumor cells, leukocytes, or lymphoid tumor cells, alone or after combination with a toxic agent to destroy these cell types, thereby treating or alleviating various malignancies or inflammatory/immune processes, and (4) identifying normal or abberrant phenomena in embryological development.

PHARMACEUTICAL COMPOSITIONS

Included within the scope of this invention are pharmaceutical compositions comprising an effective amount of E1/6 monoclonal antibody, or a fragment or conjugate thereof, or E1/6 antigen, or a fragment or conjugate thereof, and a pharmaceutically acceptable carrier. Also included within the scope of this invention are pharmaceutical compositions comprising an effective amount of one or more of the following: E1/6 monoclonal antibody, or a fragment or conjugate thereof, or E1/6 antigen, or a fragment or conjugate thereof, anti-ELAM-1, or a fragment or conjugate thereof, anti-ICAM-1, or a fragment or conjugate thereof, ELAM-1 protein, or a fragment or conjugate thereof, ICAM-1 protein, or a fragment or conjugate thereof, and ICAM-2 protein, or a fragment or conjugate thereof; and a pharmaceutically acceptable carrier.

The present invention contemplates an in vivo diagnostic procedure that comprises introducing a pharmaceutical composition of the present invention into the body of a mammal, and allowing sufficient time for the composition to localize. Humans are included within the definition of mammal. The present invention also contemplates in vitro analytical procedures employing these pharmaceutical compositions.

The pharmaceutical composition containing an effective amount of E1/6 mAb, or a fragment thereof, is expected to be useful in the treatment of a variety of pathophysiological processes, including but not limited to, melanoma tumor cell metastasis, and immunological/inflammatory diseases, particularly those involving lymphocyte-mediated tissue damage and/or graft rejection.

The ability of E1/6 mAb to recognize antigen presenting cells (noted above) indicates that a pharmaceutical composition containing a therapeutically effective amount of E1/6 may be useful in altering disease processes involving excessive immunological response to an antigen (e.g., graft rejection). E1/6 may also be useful in a diagnostic composition for the identification of these antigen presenting cells.

The monoclonal antibody or portions thereof may be useful to block tumor cell-endothelial adhesion in vivo, and thereby to inhibit metastasis.

The monoclonal antibody or portions thereof may be useful to block lymphocyte-endothelial adhesion and a lymphocyte-dendritic cell or lymphocyte macrophage adhesion in vivo, and thereby to inhibit or otherwise modify inflammatory and immune reactions. This may be particularly helpful in the treatment of automimune diseases such as lupus erythematosus, vasculitis, demyelinating diseases, and graft rejection. Monoclonal antibodies to E1/6 protein, or portions thereof, may also be useful in blocking other leukocyte types (e.g. neutrophils and monocytes) to vascular endothelium. This would be helpful in the treatment of a variety of acute and chronic inflammatory disease processes.

Monoclonal antibodies against E1/6 protein may be useful in blocking lymphoma or leukemia interactions with the vascular endothelium, and thereby to inhibit tissue spread.

Purified E1/6 protein, or portions thereof, may also be useful for the purposes stated in item 1 or 2. In addition, purified E1/6 protein, or portions thereof, by binding directly to nonlymphoid tumor cells (e.g. melanoma), leukocytes (e.g. lymphocytes), or lymphoid tumor cells (e.g. lymphoma or leukemia), may be useful alone or in combination with a toxic agent to destroy these cell types. This effect is expected be helpful in the treatment of various malignancies or inflammatory/immune processes.

Monoclonal antibodies to E1/6 protein may be utilized in the diagnostic studies, including radiologic or nuclear magnetic resonance imaging, to localize sites of altered endothelium, such as may occur in inflammation or other pathophysiological processes, including atherosclerosis.

E1/6 protein may be expressed in increased quantities in the vasculature of tumors, themselves, in which case antibodies against E1/6 protein, alone or coupled to cytotoxic agents, may be used to destroy tumor vasculature and inhibit tumor growth.

Monoclonal antibody E1/6 may be used in vitro to examine the expression of E1/6 protein in various tissue specimens to determine altered expression of this molecule that may be associated with specific disease processes (e.g. graft rejection). It may also be helpful in examining tissue or body fluids (e.g. blood, lymph, cerebrospinal fluid) for the presence of E1/6 protein, which may be increased in certain pathophysiological processes, including inflammation, immune injury, graft rejection, and certain malignancies. Monoclonal antibody E1/6 may be helpful in the diagnosis and identification of certain tumors, particularly thosed involving a prominent endothelial component (e.g. Kaposi's sarcoma)

Certain microbial organisms (e.g. viruses, rickettsia, bacteria, parasites) may interact with or infect vascular endothelium after binding to E1/6 protein. Therefore, mAb E1/6 may be useful in treating infections with these microbes by interrupting their interaction with vascular endothelium. In addition, purified E1/6 protein, or fragmants thereof, may be useful alone or in combination with toxic agents in the treatment of microbial infections by binding directly to these microbes, and helping in their elimination.

Embryological development may involve any or all of the named adhesion molecules, including E1/6 protein. MAb E1/6 and/or E1/6 protein may be useful in identifying normal or aberrant phenomena in embryological development, possibly enhancing the ability to intervene in certain developmental abnormalities or birth defects.

The conjugates of this invention may be administered in vivo in any pharmaceutically suitable carrier. A physiologic normal saline solution can be used, and may optionally include an appropriate amount of carrier protein, such as human serum albumin (for antibody stabilization). The appropriate concentration of any biologically active material in a carrier is routinely determined by practitioners in the art.

It is expected that E1/6, or fragments thereof, could be administered to a patient to treat inflammation. It is believed that E1/6 would block leukocyte adhesion to endothelium at sites of inflammation.

It is also possible to that inflammation could be blocked by administering to a patient a monoclonal antibody directed toward E1/6. The monoclonal antibodies could also comprise antibody fragments, for example, $F(ab')_2$ fragments, which minimize immunological reaction due to the Fc portion of the immunoglobulin.

Adminstration of E1/6, or a fragment thereof, may also be useful for the prevention of post-reperfusion injury. When treating arterial thrombosis, induction of reperfusion by clot lysing agents, such as tissue plasminogen activator (t-PA), is often associated with tissue damage. Such tissue damage is thought to be mediated, at least in part, by leukocytes. Therefore, administration of E1/6, or a fragment thereof, preferably, a leukocyte-binding fragment, would be expected to block leukocyte-endothelial interactions, and thereby diminish or prevent post-reperfusion injury.

The E1/6 molecule, or fragment thereof, or antibodies and antibody fragments directed to E1/6, can be formulated into pharmaceutically useful compositions according to known methods, such as by admixture with a pharmaceutically acceptable carrier vehicle. Suitable vehicles and their formulation are described, for example, in *Remington's Pharmaceutical Sciences* (16th ed.), Osol, A. (ed.), Mack Publishers, Easton (1980). In order to form a pharmaceutically acceptable composition suitable for effective administration, such compositions will contain a therapeutically effective amount of the E1/6 protein, or fragment thereof, or antibody or antibody fragment directed to E1/6, either alone or with a suitable amount of carrier vehicle.

When used for the treatment of metastasis, immune responses, inflammation, graft rejection, post-reperfusion injury, leukemia, lymphoma bacterial infection, vasculitis, or inhibition of the metastatic spread of tumor cells, it is expected that the pharmaceutical composition may comprise from 1 pg/kg to 10 mg/kg patient of E1/6, fragment of E1/6, or fusion protein of the invention, although higher or lower doses are possible. When used for the purpose of treating inflammation/immune responses, metastasis or infections, the pharmaceutical composition may comprised from 1 pg/kg to 10 mg/kg of E1/6-specific antibody or antibody fragment therof, although higher or lower doses are possible.

Additional pharmaceutical methods also may then be employed to control the duration of action. Controlled release preparations may be achieved by the use of polymers to complex or absorb the E1/6 protein, E1/6 fragment or antibody or antibody fragment directed to E1/6 protein of the invention. Controlled delivery may be achieved by selecting appropriate macromolecules (for example, polyesters, polyamino acids, polyvinyl pyromolidone, ethylenevinylacetate, methylcellulose, carboxymethylcellulose, protamine sulfate, or lactide/gylcolide copolymers). The rate of drug release may also then be controlled by altering the concentration of such macromolecules. Another possible method for controlling the duration of action comprises incorporating the therapeutic agents into particles of a polymeric substance such as polyesters, polyamino acids, hydrogels, polylactide/glycolide copolymers, or ethylenevinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences* (1980).

The compositions of the present invention may be administered in any convenient method for introducing foreign substances into the blood stream of mammals. The pharmaceutical compositions of the present invention may be diluted with conventional pharmaceutical carriers for administration into the subject. Intravenous injection is preferred. Also included within the scope of this invention is administration of the pharmaceutical composition orally, intranasally, subcutaneously, intramuscularly, intra-arterially, or parenterally. The pharmaceutical composition may be included in a liposome, as disclosed in U.S. Pat. No. 4,522,803.

If an antibody conjugate of this invention is to be used in vivo, a gamma or positron emitting radionucleotide can be linked to the conjugate. The choice of the particular element and its use is within the skill of the art. Examples of radioisotopes include, but are not limited to, $^{3}H$, $^{125}I$, $^{32}p$, $^{35}S$, and $^{14}C$.

E1/6 mAb, or a fragment thereof, or E1/6 protein, or a fragment thereof, may be useful coupled to a chemotherapeutic reagent capable of binding to tumor cells that express E1/6 receptors. The coupled reagent is expected to be of killing tumor cells, particularly melanoma tumor cells. The method for treating melanoma tumor cells would comprise administering to a patient a pharmaceutical composition comprising an effective amount of mAb E1/6, or a fragment thereof, or E1/6 protein, or a fragment thereof, coupled to an anti-tumor agent. Anti-tumor agents include, but are not limited to diptheria toxin, ricin toxin, ricin A chain toxin, or lectin toxin. Such anti-tumor agents coupled to an antibody or antigen are disclosed in U.S. Pat. No. 4,675,382.

DIAGNOSTICS

Included within the scope of this invention is the use of E1/6 mAb, or fragments thereof, or E1/6 protein, or fragments thereof, in in vivo or in vitro, diagnostic methods.

The literature has an extensive repertoire of groups that may be used to link almost any functionality through an amino functionality to a solid surface. U.S. Pat. No. 3,817,837 describes a large number of functionalities that may be used for linking proteins or haptens to amino functionalites, which disclosure is herein incorporated by reference. Other references that show linking to affinity columns, surfaces for apheresis, surfaces for diagnostics, surfaces for chromatography, surfaces for reaction and the like may be found in references cited in catalogs such as the BRL catalog, Bio-Rad catalog, Sigma catalog, Pierce catalog, Pharmacia catalog, etc. It is evident that the particular manner in which E1/6 mAb, a fragment or conjugate thereof, E1/6 antigen, or a fragment or conjugate thereof, is bound to the surface may be varied widely. In particular situations, one spacer arm may be selected over another because of particular properties.

The antibody linked to a solid substrate allows for orientation of immunoglobulins, either as $F(ab')_2$ fragments or Fab' fragments, or as intact immunoglobulins. For example, the amino groups of a substrate may be iodoacetylated, followed by reaction with the available mercapto groups of the truncated immunoglobulin. Alternatively, the intact immunoglobulins may be oxidized with a glycol cleaving agent, e.g. periodate, and the resulting dialdehyde reacted with an amino group or hydrazine to form a Schiff base or imine.

Diagnostics involving binding the antibody or antigen of the present invention to a solid surface is for the most part referred to as heterogeneous, in that these processes involve a separation step, though there is an increasing number of diagnostic protocols where a solid surface is involved without the necessity for a separation step. In diagnostics, there may be of interest the binding of members of a specific binding pair, comprising ligand and receptor, which bind to form a complex, where the homologous members of the specific binding pair have a high association constant for each other, usually greater than $10^8$ l/mol.

The haptens will generally be from about 150 to 5000 daltons, usually up to about 2000 daltons and may include naturally occurring hormones, naturally occurring drugs, synthetic drugs, pollutants, affector molecules, growth factors, lymphokines, amino acids, oligopeptides, chemical intermediates, nucleotides, oligonucleotides or the like. Diagnostics for such compounds may be in the detection of drugs of abuse, therapeutic dosage monitoring, health status, detection of disease, e.g. endotoxins, and the like. Proteins are of interest in a wide variety of diagnostics, such as detecting cell populations, blood type, pathogens, immune responses to pathogens, immune complexes, saccharides, naturally occurring receptors, and the like. Receptors may find use in binding to haptens, proteins, other receptors, or the like, or detection of the presence of pathogens, the level of a particular protein in a physiological fluid, the presence of haptens in a wide variety of samples, such as physiological fluids, air, process streams, water, etc. Nucleic acids may also find use in the detection of proteins specifically binding to nucleic acids, complementary strands, and the like.

A large number of protocols exist for detecting the various analytes of interest. The protocols may involve use of a signal producing system, which involves a labeled conjugate, which may be directly or indirectly detected. These techniques may employ dyes, enzymes, enzyme substrates or co-factors, enzyme inhibitors, fluorescers, chemiluminescers, particles, or the like.

For the purposes of the present invention, the label should provide a signal related to the presence of analyte in the sample which results in the detection of electromagnetic radiation, particularly light in the ultra-violet, visible or infrared range. By use of the subject solid substrate, the light may be detected through the solid substrate, rather than requiring reflection, which is normally subject to significant error. In addition, techniques involving total internal reflection may be employed, as described in U.S. Pat. No. 3,939,350. Other patents of interest, both domestic and foreign, which describe protocols of interest include U.S. Pat. Nos. 3,654,090; 3,850,752; 4,347,312; EPA 2,963, and references cited therein.

Assays can be carried out in accordance with the various protocols. In accordance with the subject invention, the sample is contacted with a solid substrate and various operations may be carried out, such as the addition of various reagents, incubations, washings, and the like. The final result of the assays will be the change in the amount of a product that absorbs or produces light, either by light absorption or by light emission in relation to the presence or amount of the analyte of interest. Usually, this is as a result of formation of a specific binding pair, where one of the members may serve as a bridge to form a sandwich, or there may be a single complex, or complexes may be bound to complex binding proteins, such as *S. aureus* protein A. rheumatoid factor, immunoglobulins specific for immune complexes, or the like.

By having fluorescent markers, such as fluorescent particles, fluorescent conjugated antibodies, or the like, the sample may be irradiated with light absorbed by the fluorescers and the emitted light measured. For example, where one has microtiter wells, one can measure the fluorescent light emitted through the sides of the well, substantially minimizing the background resulting from the activating light. Where dyes are employed as the label or produced as a result of a reaction, e.g. an enzymatically catalyzed reaction, the light may be transmitted through the sample and the container and measured as an indication of the presence of the analyte, since there is a relatively low level of absorption by the container. Thus, highly sensitive assays can be employed with the subject system. Also included within the scope of the present invention are avidin-biotin detection and diagnostic systems. These protocols are well known to practitioners in the art.

Monoclonal antibody E1/6, or a fragment thereof, may be linked to a solid substrate to serve as catching antibodies, in the detection of pathogens. The sample would then be added and cells having the epitope recognized by the antibody would bind to the antibody on the surface. Non-specifically bound cells are washed away leaving substantially only specifically bound cells. Labeled monoclonal antibodies are then added to the container that are specific for an epitope other than the epitope recognized by the catching antibody. After incubating to allow reaction between the antibodies, and cells, non-specifically bound antibodies are washed away and the presence of the label determined.

A variation would be to employ E1/6 antigen recognized by a cell receptor. The antigen would be bound to the surface to catch the cells and a labeled antigen used to label the cells. The receptor could be surface immunoglobulin (sIg). In this way the presence of the specifically bound cells could be determined, whereby having the antigen of interest complementary to the receptor bound to the surface, cells having the sIg specific for such antigen could be determined. Instead of having antigen, one would have antibodies to the antigen bound to the surface to non-covalently bind the antigen to the surface.

The subject antigen and antibody may be linked to solid substrates and used for affinity columns, chromatographs, or the like, where the antigen or antibody bound to the surface and complex formation or other binding event can be detected. With these solid substrates, one can visually observe along the length of a column in order to determine the particular site at which complex formation occurs. This technique can also be used for diagnosis, where different antigens or receptors may be bound at different sites along the column, followed by introducing the sample through the column, followed by adding the signal producing system, e.g. enzyme bound specific binding pair member and developer, and detecting the areas of color formation.

The antibody or antigen bound to a solid substrate may be used for a variety of other purposes, wherever one wishes to provide a high density of oriented molecules at a surface or visualize events or provide for ready transmission of light, where a substance is non-diffusively bound to solid surface.

It has also been shown that proteins, antibodies, or antibody fragments can be coupled to metal sol particles in order to produce a conjugate useful in electron microscopy (Leuvering, U.S. Pat. No. 4,313,734).

It has also been shown that tumors can be localized by injecting a first labeled antibody or antibody fragment, followed by injection of a second unlabeled antibody specific for the first antibody's label (Goldenberg, U.S. Pat. No. 4,624,846).

The invention also relates to a method of detecting endothelial cell activation in a patient by an assay for E1/6, comprising contacting a detectably labeled antibody directed to E1/6 with a sample suspected of containing E1/6 or cell that expresses E1/6 on its surface, and detecting whether a complex has formed.

The detection and quantitation of antigenic substances and biological samples frequently utilize immunoassay techniques. These techniques are based upon the formation of a complex between the antigenic substance being assayed, e.g, E1/6, and an antibody or antibodies in which one or the other member of the complex may be detectably labeled. In the present invention, the E1/6 specific antibody may be labeled with any conventional label.

Physiological processes that involve endothelial activation include, but are not limited to inflammation, tissue repair, and other pathophysiological processes that promote focal attachment of tumor cells to vessel (vascular) walls.

All publications and patent application mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

Example 1

The following cells were maintained as described below. Human umbilical vein endothelial cells (HEC) were serially passaged in Medium 199 (M. A. Bioproducts, Bethesda, Md.) supplemented with 20% fetal calf serum (FCS, Gibco Laboratories, Grand Island, N.Y.), endothelial cell growth factor (50 ug/ml, Biomedical Technologies, Inc., Stoughtom, Mass.), and porcine intestinal heparin (50–100 ug/ml, Sigma Chemical Co., St. Louis, Mo.). Confluent HEC monolayers (subculture) grown in microtitier wells (Cluster 96, Costar, Cambridge Mass.) precoated with 0.1% gelatin (Difco, Detroit, Mich.) were used for adhesion assays. The human dermal fibroblast cell line AlF21 (provided by Dr. J. Rheinwald, Dana-Farber Cancer Institute, Boston, Mass.) was maintained in Medium 199 with 15% fetal calf serum. Human tumor cell cultures were obtained from the American Type Culture Collection (Rockville, Md.), maintained in recommended media, and passaged weekly using trypsin/versene (M. A. Bioproducts).

Example 2

Balb/C female mice were immunized with HEC that had been exposed to recombinant tumor necrosis factor alpha (TNF, gift of Biogen Corp, Cambridge, Mass.) for 24 hr, and harvested nonenzymatically (2 mM EDTA, 1% bovine serum albumin, 15 min, 37° C.). Fusion of splenocytes with NS-1 myeloma cells was performed as described in the detailed description. mAb E1/6 (IgG1) was selected on the basis of increased binding to TNF-activated HEC in an indirect radioimmunoassay. The hybridoma was cloned and maintained in RPMI-1640 (M. A. Bioproducts) supplemented with 10% horse serum MEM nonessential amino acids (100 uM), and MEM sodium pyruvate (1 mM) (Gibco).

Example 3 Comparative

Previously generated mAbs, including H18/7 (IgG2a), which recognized the inducible HEC surface molecule designated ELAM-1, mAbs E1/1 (IgG2b) and H4/45 (IgG1), which recognize a $M_r$ 96,000, constitutively expressed HEC/mesenchymal cell surface molecule, and two nonbinding mAbs (K16/16, IgG1; E1A, IgG2a) were employed in comparative studies. mAb LB-2 (IgG2a), which recognizes ICAM-1, was the gift of Dr. E. Clark, University of Washington, Seattle, Wash.

Pretreatment of the melanoma cells with mAb E1/6 followed by washing did not block adhesion, whereas pretreatment of endothelial cells was effective (34±7% inhibition of Hs 294T cell adhesion, 2 experiments). Further, mAb E1/6 did not significantly inhibit (<5%) the adhesion of Hs 294T cells to the subendothelial matrix exposed after nonenzymatic removal of HEC (2 mM EDTA).

Figure 2B:
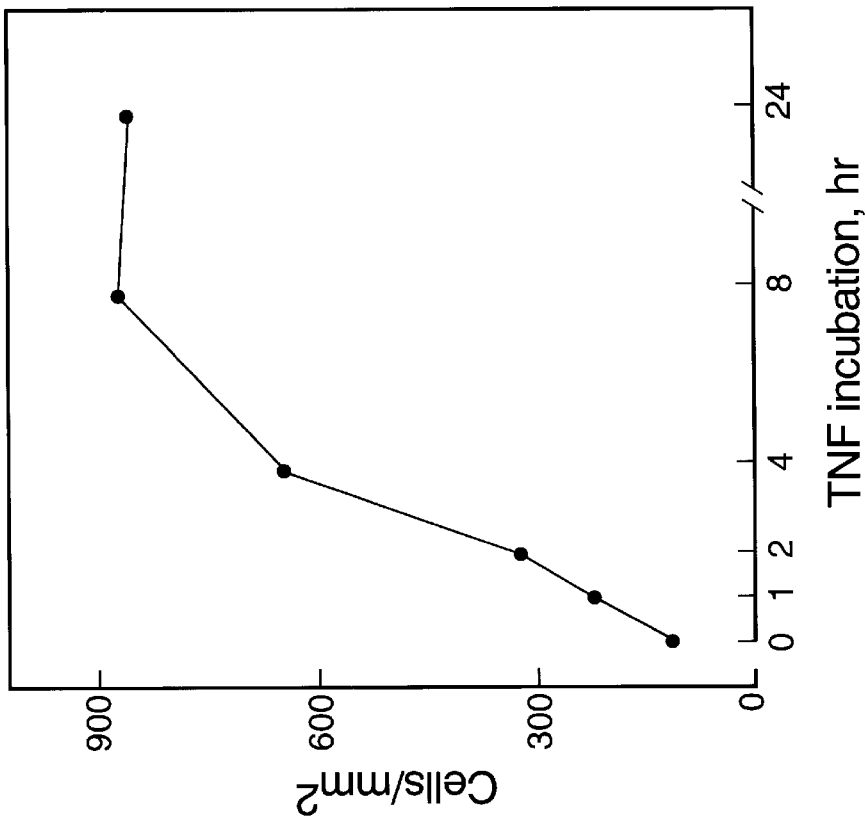
FIG. 2A–B shows the comparison of mAb surface binding and melanoma cell adhesion. (A) HEC surface expression of E1/6 protein, ELAM-1, and ICAM-1. (B) Hs 294T adhesion to TNF-activated HEC.

Treatment of HEC monolayers with anti-ELAM-1 monoclonal antibodies (mAbs H18/7 and H4/18 alone and in combination), at concentrations up to 100 times greater than those effective in inhibiting leukocyte-HEC adhesion, did not reduce the adhesion of Hs 294T or MEL-24 cells to IL-1 or TNF-activated HEC (mAb MEL-24 cells to IL-1-stimulated HEC: 14±6% increase in Hs 294T adhesion, N=2, 7% increase in MEL-24 adhesion, N=1). A second cytokine-inducible endothelial cell surface protein, ICAM-1, appears to play a role in lymphocyte adhesive interactions. The time course of ICAM-1 expression on activated HEC is similar to that of increased tumor cell adhesion (FIG. 2B). The mAb LB-2 (provided by Dr. E. Clark, University of Washington, Seattle, Wash.) that recognizes ICAM-1 failed to inhibit melanoma-endothelial cell adhesion (with IL-1-stimulated HEC: 4±8% increase in Hs 294T adhesion, N=3, 2±7% decrease in MEL-24 adhesion, N=2; with TNF-stimulated HEC: 7±6% increase in Hs 294T adhesion, N=4; 6±5% increase in MEL-24 adhesion, N=2). These negative data imply that the epitopes on ELAM-1 and ICAM-1 recognized by these monoclonal antibodies are not involved in the increase tumor cell-HEC adhesion observed in this study.

Example 4

Cell Adhesion Assays. HEC monolayers were pretreated for up to 48 hours with IL-1 (5 U/ml), TNF (200 U/ml), or with bacterial endotoxin (1 ug/mil in M199-20% FCS with endothelial growth factor and heparin). After cytokine or endotoxin pretreatment, the HEC monolayers were incubated for 30–45 min (37° C.) with mAbs (neat culture supernatant or dilutions of ascites protein at 10 ug/ml in RPMI-10% horse serum). Tumor cells were labeled with [$^{35}$S] cysteine and methionine, resuspended, washed, and added to HEC monolayers (6–8×10$^4$ cells per microtiter well; mAb-containing supernatants were not routinely removed). After 30 minutes at 25° C., plates were sealed with acetate tape covers (Plate sealers, Dynatech, Alexandria, Va.), inverted, and centrifuged (150×g, 5 min) to remove nonadherent cells. Cellular contents were solubilized (0.1% SDS, 0.01% NaOH) and counted in a liquid scintillation counter.

TABLE 1

Percent inhibition of tumor cell-endothelial adhesion by mAb E1/6.*
HEC Pretreatment 6 hr

| Cell line+ | Control | IL-1 | TNF | Endotoxin |
|---|---|---|---|---|
| MEL-24 | 54 ± 7 | 67 ± 9 | 71 ± 7 | 70 ± 3 |
| (n) | (5) | (3) | (5) | (3) |
| Hs 294T | 29 ± 11 | 63 ± 7 | 60 ± 5 | 60 ± 12 |
| (n) | (3) | (3) | (3) | |
| HT-29 | 5 ± 10 | −2 ± 18 | 8 ± 3 | N.D. |
| (n) | (2) | (2) | (2) | |

*HEC monolayers were incubated for 6–8 hr in M199–20% fetal calf serum, alone (control) or supplemented with IL-1 (5 U/ml), TNF (200 U/ml), or endotoxin (1 ug/ml). Cultures were then washed and incubated for 30 min in RPMI-10% horse serum alone, E1/6 culture supernatant, or with control mAbs. Data represented as percent decrease (mean ± SEM, n experiments) in adhesion of tumor cells to HEC exposed to mAb E1/6 compared to no mAb. Control mAb, which bound to HEC monolayers, had no significant effect on tumor cell adhesion to unstimulated or stimulated HEC.

FIG. 1 shows the effect of mAbs E1/6, H18/7 (anti-ELAM-1) and LB-2 (anti-ICAM-1) on MEL-24 cell adhesion to HEC. Unstimulated and TNF-stimulated HEC monolayers were exposed to medium containing no mAb E1/6 (culture supernatant), mAb H18/7 (10 ug/ml), or mAb LB-2 (10 ug/ml) for 30 min at 37° C. prior to the adhesion assay. Bars represent mean ± SEM of quadruplicate microtiter wells one of four similar experiments.

Example 5

Comparison of mAb surface binding and melanoma cell adhesion is shown in FIG. 2. (A) HEC surface expression of E1/6 protein, ELAM-1, and ICAM-1. HEC monolayers were pretreated with TNF (200 U/ml) for various times, and exposed to mAbs E1/6, H18/7 (anti-ELAM-1), or LB-2 (anti-ICAM-1) at 4° C. mAb cell surface binding was assessed using [$^{125}$I-labeled anti-mouse immunoglobulin F(ab')$_2$. Specific counts were determined by subtracting cpm determined with irrelevant, isotype matched mAbs (generally less than 10$^3$ cpm). Each data point represents the mean of quadruplicate wells. (B) Hs 294T adhesion to TNF-activated HEC. HEC were pretreated with TNF for various times, washed, and exposed to mAb E1/6 (30 min, 37° C.) prior to a 30 min adhesion assay. Data represent means of quadruplicate microtiter wells. The radioimmunobinding and adhesion studies were performed simultaneously using matched HEC cultures.

Example 6

Cell Surface Immunobinding Studies. Confluent HEC monolayers were treated (for up to 48 hr) with recombinant interleukin-1 β (IL-1, 5 U/ml, Biogen), or bacterial endotoxin (1 ug/ml, E. coli serotype No. 055:B5, Sigma) in Medium 199 with 20% FCS. HEC were washed with RPMI-10% FCS, and exposed to mAbs (100 ul/well) for 1 hour at 4° C. Monolayers were washed 3 times with cold RPMI-10% calf serum (Gibco), and exposed to [$^{125}$I] sheep anti-mouse F(ab')$_2$ immunoglobulin fragments (New England Nuclear, Cambridge, Mass., 1:10% calf serum) for an additional 1 hour at 4° C. HEC were washed 4 times, solubilized (0.1% SDS in 0.01% NaOH), and radioactivity was determined using a Beckman gamma counter. mAbs K16/16 (IgG1) and ElA (IgG2a), which do not recognize basal or stimulated HEC, were employed as negative controls, and for determination of nonspecific binding.

Example 7

Radiolabelling and immunoprecipitation. HEC monolayers were incubated in the presence of [$^{35}$S] L-cysteine and L-methionine (New England Nuclear) for up to 6 hours with or without TNF as previously described. HEC were nonenzymatically suspended (2 mM EDTA in Hanks' BSS with 1% bovine serum albumin, washed twice, lysed using 2 mM Tris HCL plus 2% Nonidet P-40 and 1 mM phenylmethylsufonyl fluoride (pH 7.4, 30 min, 4° C.), and centrifuged (10,000×g, 10 min, Eppendorf, Brinkmann) to remove cellular debris. For immunoprecipiation, HEC lysates (50–100 ul) were incubated for 12–16 hours at 4° C. with E1/6 hybridoma culture supernatant (equal volume) or ascites preparations (5 ug). Samples were subsequently incubated with anti-mouse immunoglobulin bound to Sepharose-4B (2 hr, 4° C., Cooper Biomedicals, Malvern, Pa.) which had been pretreated for 12–16 hours with lysates of unlabeled, unstimulated HEC. Beads were washed, boiled in buffer containing 0.5 mM sodium dodecyl sulfate and 0.1 mM 2-mercaptothanol, and electrophoresed using a 4–11% sodium dodecyl sulfate/polyacrylamide gel (NaDodSO$_4$/PAGE). Gels were dried and autoradiographed for 2–7 days at −70° C. HEC monolayers were exposed to control medium or to medium containing TNF (200 U/ml) in the presence of [$^{35}$S] amino acids for 5 hr. After immunoprecipitation, samples were electrophoresed using a 4–11% NaDodSO$_4$/polyacrylamide gel, and autoradiographed. mAbs E1/6, H18/7 and LB-2 precipitated proteins in TNF-stimulated HEC. mAb E1/6, which recognized a constitutively expressed antigen, reacted with a labeled species in both control and activated endothelium (not shown).

Example 8

Tissue Immunostaining. Certain normal and pathologic tissues were selected from fresh surgical or autopsy material in the Department of Pathology, Brigham and Women's Hospital, and frozen, using dry ice/isopentane. Frozen sections (4–6 um) were air dried, and fixed in acetone (3–10 min, 4° C., pH 7.3) supplemented with 4% swine serum, and exposed to primary antiserum at 25° C. for 30–45 minutes, followed by peroxidase-conjugated rabbit anti-mouse immunoglobulin (Dako Corp., Santa Barbara, Calif.; absorbed reagent, 1:80 dilution in Tris buffer with 1% swine serum), and peroxidase-conjugated swine antibodies to rabbit immunoglobulin (Dako; 1:60 dilution in Tris buffer). In some studies, an avidin-biotin system (ABC Elite, Vector Laboratories, Burlingame, Calif.) was employed. A peroxidase rection was carried out using 1 ug/ml 3,3'-diaminobenzidine tetrahydrochloride (Aldrich Chemical Co., Milwaukee, Wis.) in 0.05 Tris buffer with 0.03% hydrogen peroxide as chromogen.

Example 9

Figure 2A:
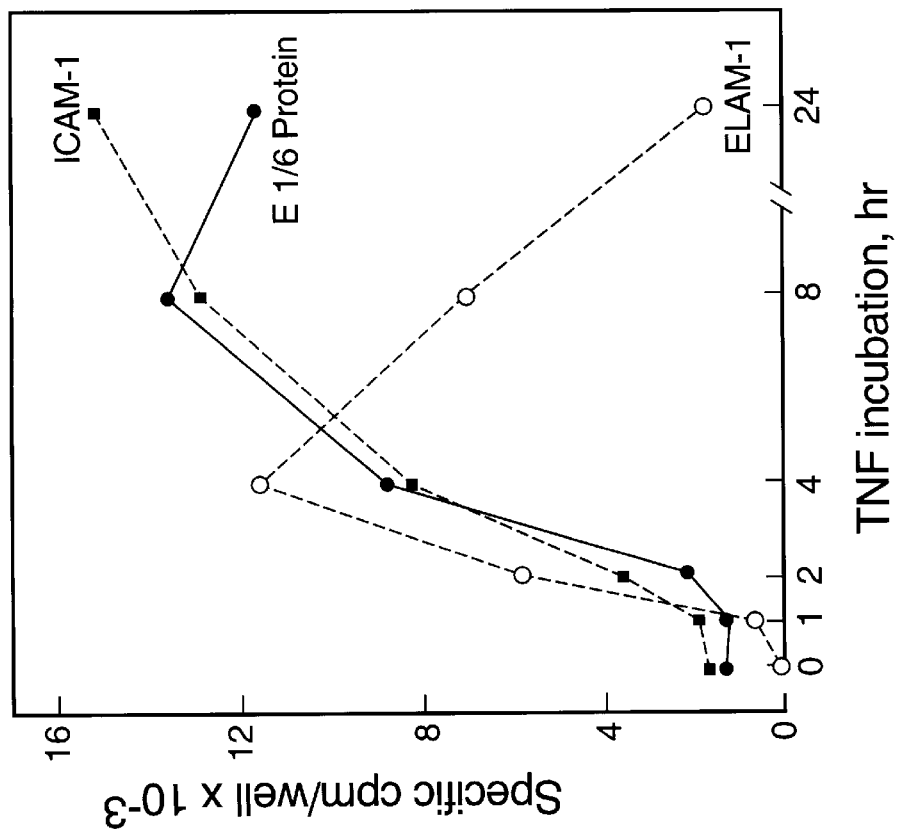

Cell Surface Expression of E1/6 Antigen in Vitro. E1/6 antigen is present on the surface of intact, unstimulated HEC monolayers as detected in an indirect immunobinding assay (FIG. 2A). Continuous exposure of HEC monolayers to IL-1 or endotoxin resulted in increased binding of mAb E1/6, detectable at 2 hours, maximal at 6–8 hours (13.6±1.9 -fold increase, 6 experiments), and remaining elevated through 48 hours. Similar results were observed with IL-1 or endotoxin treatment of HEC monolayers (data not shown). E1/6 antigen expression in activated HEC differs significantly from ELAM-1 expression, which is maximum at 4 hours and declines toward basal levels by 24 hours (FIG. 2A). In contrast, the kinetic patterns of E1/6 antigen and ICAM-1 expression in activated HEC are quite similar (FIG. 2A). Interferon gamma (IFN -, Collaborative Research, Beford, Mass.) also induced increased expression of endothelial E1/6 antigen, although at later times and to a lesser degree than observed with IL-1, TNF, or endotoxin. Specific binding of mAb E1/6 to IFN- treated HEC monolayers was increased 1.7±0.3 - fold (n −2) after 24 hr, and 3.0±0.3 - fold (n −2) after 48 hr. In three experiments, the human dermal fibroblast cell line AlF21 (unstimulated or cytokine stimulated) expressed little or no E1/6 antigen or ELAM-1, but did express ICAM-1 (not shown). No significant expression of E1/6 antigen was detected on melanoma cells (MEL-24 or Hs 294T) in indirect radioimmunoassays, immunoperoxidase studies, or flow cytometric anaylsis (not shown).

Example 10

Immunochemical Characterization of E1/6 Protein. mAb E1/6 failed to react with COS cells transfected with cDNAs that encode ELAM-1 as detected by immunoperoxidase staining (not shown). In indirect immunoprecipation experiments using total cell extracts from biosynthetically labeled TNF-stimulated HEC, mAb E1/6 antigen and ICAM-1 are expressed on unstimulated HEC (cell surface radioimmunoassay, FIG. 2A), biosynthetically labeled polypeptides were not detected by immunoprecipitation from unstimulated HEC lysates, possibly reflecting low basal synthetic rates. After treatment of the HEC precipitate with N-Glycanase (N-glycosidase F, Genzyme, Boston, Mass.; 10 U/ml, 118 hr), a single band corresponding to a polypeptide of $M_r$ 70,000 was observed (not shown).

Example 11

In Vivo Expression of E1/6 protein. Frozen sections of human tissues stained with an immunoperoxidase technique were utilized to investigate the expression of E1/6 reacted with vascular endothelium in numerous vessels, notably venules and arterioles, but not with smooth muscle or other non-endothelial components. Reactivity was noted in vessels of normal skin (n−2) and brain (n−2); strong reactivity was observed in endothelial cells within venules of inflamed skin (insect bite reaction, n−1), suggesting that upregulation of E1/6 protein can occur in vivo.

The expression of E1/6 protein can be increased in vitro by multifunctional cytokines such as IL-1 and TNF, which are produced by a variety of cell types, including macrophages, vascular endothelium, smooth muscle, and certain tumor cells themselves. In additon, mAb E1/6 reacted strongly with endothelium in a sample of inflamed skin, suggesting that upregulation of this protein also occurs in vivo.

In regard to E1/6 protein, initial studies suggest that mAb E1/6 inhibits adhesion of certain lymphoid cells to activated endothelium suggesting that E1/6 protein may function as an endothelial-lymphocyte adhesion molecule. ELAM-1, which mediates endothelial adhesion of polymorphonuclear leukocytes, may also support adhesion of the colon carcinoma cell line. In two experiments, anti-ELAM-1 mAb H18/7 blocked HT-29 cell adhesion to TNF-activated HEC monolayers by 71±7%, while mAb E1/6 had little or no effect. These studies raise the possibility that distinct endothelial surface proteins mediate the adhesion of different tumor cell types.

HEC monolayers were pretreated for 1 hr with TNF (200 U/ml) in M199-20% fetal calf serum, washed, and incubated for an additional 30 min in RPMI-1640 without L-cysteine and L-methionine, supplemented with 10% dialyzed fetal calf serum and TNF. [$^{35}$S]L-cysteine and methionine were then added for 15 or 30 min ("pulse"). Certain samples were lysed immediately, while others (30 min labeling) were washed and placed in M199-20% fetal calf serum with TNF for various times before lysis. "Kilietic labeling ("pulse chase") of E1/6 protein was observed."

Example 12

Figure 3:
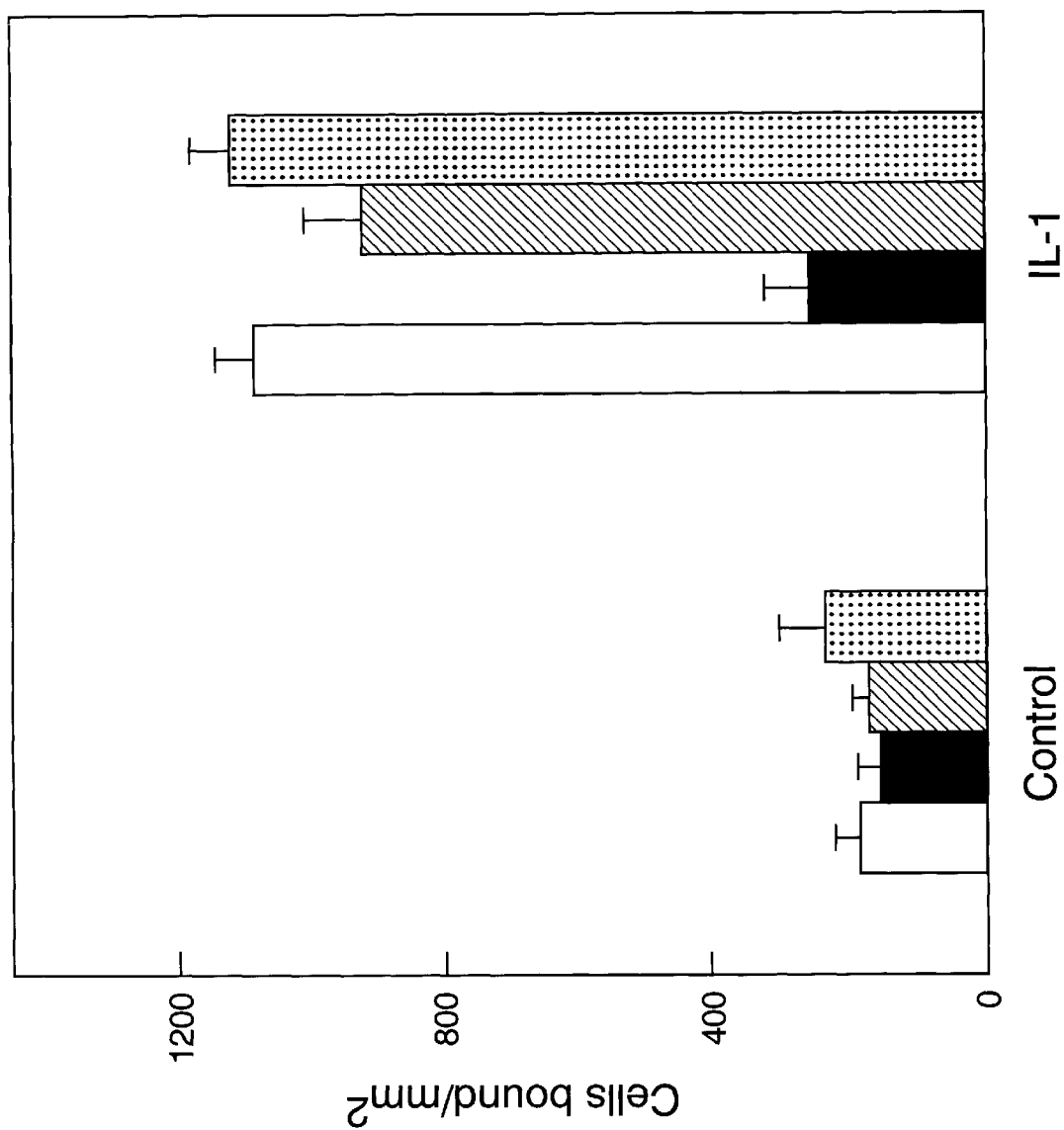
FIG. 3 shows the inhibition of adhesion of Ramos cells to activated endothelium by E1/6 mAb.

FIG. 3 shows the adhesion of Ramos cells to activated endothelium is inhibited by antibody E1/6. Vascular endothelium cultured in microtiter wells was exposed to medium containing no cytokine (Control) or to recombinant interleukin-1 beta (IL-1) for 6 hr at 37° C. Burkitt's lymphoma (Ramos) cells were fluoresceinated, and added to assay wells (200,000 cells per well) and allowed to settle onto the endothelial monolayers (20 min, 25° C.). The microtiter plates were then sealed with acetate tape cover, inverted, and centrifuged (approx. 150 ×g, 5 minutes) to remove nonadherent cells. Medium was drained from the wells, and the contents solubilized (SDS) and counted on a fluorescence concentration analyzer. Results are expressed as number of adherent Ramos cells per mm$^2$ of endothelia monolayer (calculated from total fluorescence of an aliquot of known cell number, and the surface area of the microtiter well floor).

Open - No antibody
Solid - mAb E1/6
Diagonal - mAb H18/7 (anti-ELAM-1)
Dotted - mAb LB-2 (anti-ICAM-1)

FIG. 4 shows that the adhesion of peripheral blood lymphocytes is partially blocked by monoclonal antibody E1/6, and by a monoclonal antibody to ICAM-1 (mAb El/7). Combination of mAb E1/6 and mAb E1/7 produced more substantial inhibition of adhesion than either reagent alone. Peripheral blood lymphocytes were prepared from normal donors by density gradient centrifugation (Ficoll). The preparation was depleted of monocytes by adhesion to gelatin/plasma-coated tissue culture plastic (two cycles), with the resultant population containing a majority of T-cells, together with B-cells, NK cells, etc. Endothelium was pretreated with cytokines and the assay carried out as described in the first example.

Open - No antibody
Solid - mAb E1/6
Diagonal - mAb E1/7 (anti-ICAM-1)
Dotted - mAb E1/6+mAb E1/7

We claim:

1. A monoclonal antibody E1/6 having the ATCC accession number HB 11105 or an antigen binding fragment thereof, said antibody or antigen binding fragment thereof being characterized by its ability to block in vitro;

a) tumor cell endothelial adhesion, b) lymphocyte endothelial adhesion, c) lymphocyte adhesion to or interaction with antigen presenting cells, d) leukocyte cell adhesion to vascular endothelium, or e) lymphoid tumor cell endothelial adhesion.

2. The monoclonal antibody of claim 1 wherein said antigen presenting cells are selected from the group consisting of dendritic cells, macrophages, and endothelial cells.

3. A monoclonal antibody E1/6, or an antigen binding fragment thereof, said antibody or fragment being conjugated to a ligand or chelating agent.

4. A monoclonal antibody E1/6 having the ATCC accession number HB 11105 or an antigen binding fragment thereof.

* * * * *